United States Patent
McDowall

(10) Patent No.: US 10,743,754 B2
(45) Date of Patent: *Aug. 18, 2020

(54) ANGLED ENDOSCOPE TIP IMAGE CAPTURE UNIT

(71) Applicant: INTUITIVE SURGICAL OPERATIONS, INC., Sunnyvale, CA (US)

(72) Inventor: Ian E. McDowall, Woodside, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/507,717

(22) Filed: Jul. 10, 2019

(65) Prior Publication Data

US 2019/0328219 A1    Oct. 31, 2019

Related U.S. Application Data

(63) Continuation of application No. 15/126,952, filed as application No. PCT/US2015/020890 on Mar. 17, 2015, now Pat. No. 10,390,689.

(Continued)

(51) Int. Cl.
*H04N 13/00* (2018.01)
*A61B 1/05* (2006.01)
(Continued)

(52) U.S. Cl.
CPC .......... *A61B 1/05* (2013.01); *A61B 1/0011* (2013.01); *A61B 1/00096* (2013.01);
(Continued)

(58) Field of Classification Search
CPC .......... A61B 1/00096; A61B 1/0011; A61B 1/00179; A61B 1/00193; A61B 1/05; G02B 23/2415
(Continued)

(56) References Cited

U.S. PATENT DOCUMENTS

| 5,797,836 A | 8/1998 | Lucey et al. |
| 6,038,079 A | 3/2000 | Michaels |

(Continued)

FOREIGN PATENT DOCUMENTS

| CN | 1481753 A | 3/2004 |
| EP | 2143374 B1 | 7/2013 |

(Continued)

OTHER PUBLICATIONS

Hagen N., et al., "Foveated Endoscopic Lens," Journal of Biomedical Optics, Feb. 2012, vol. 17 (2), pp. 021104-1-021104-6.
International Preliminary Report on Patentability for Application No. PCT/US15/20890, dated Sep. 29, 2016, 10 pages.
International Search Report and Written Opinion for Application No. PCT/US15/20890, dated Jun. 25, 2015, 13 pages.

(Continued)

*Primary Examiner* — Gims S Philippe
(74) *Attorney, Agent, or Firm* — Meunier Carlin & Curfman LLC

(57) ABSTRACT

A family of endoscopes includes a non-zero degree endoscope and a zero degree endoscope. The zero degree endoscope includes a first image capture unit mounted in a distal portion of the zero degree endoscope with a lengthwise axis of the first image capture unit substantially parallel to a lengthwise axis of that distal portion. The non-zero degree endoscope includes a second image capture unit mounted in a distal portion of the non-zero degree endoscope with a lengthwise axis of the second image capture unit intersecting a lengthwise axis of that distal portion at a non-zero angle. The first and second image capture units have substantially identical non-folded optical paths.

20 Claims, 8 Drawing Sheets

Related U.S. Application Data

(60) Provisional application No. 61/954,300, filed on Mar. 17, 2014.

(51) Int. Cl.

| | | |
|---|---|---|
| *A61B 1/00* | (2006.01) | |
| *G02B 23/24* | (2006.01) | |
| *H04N 5/225* | (2006.01) | |
| *H04N 13/254* | (2018.01) | |
| *H04N 13/296* | (2018.01) | |

(52) U.S. Cl.
CPC ...... *A61B 1/00179* (2013.01); *A61B 1/00193* (2013.01); *G02B 23/243* (2013.01); *G02B 23/2415* (2013.01); *G02B 23/2423* (2013.01); *G02B 23/2469* (2013.01); *G02B 23/2484* (2013.01); *H04N 5/2253* (2013.01); *H04N 13/254* (2018.05); *H04N 13/296* (2018.05); *H04N 2005/2255* (2013.01); *H04N 2213/001* (2013.01)

(58) Field of Classification Search
USPC .......................................................... 348/47
See application file for complete search history.

(56) References Cited

U.S. PATENT DOCUMENTS

| | | | |
|---|---|---|---|
| 6,635,010 | B1 | 10/2003 | Lederer |
| 7,027,231 | B2 | 4/2006 | Miyano |
| 7,869,140 | B2 | 1/2011 | Duckett et al. |
| 8,771,177 | B2* | 7/2014 | Hale .................. A61B 1/00009 600/109 |
| 10,390,689 | B2 | 8/2019 | McDowall |
| 2002/0103420 | A1 | 8/2002 | Coleman et al. |
| 2003/0163029 | A1* | 8/2003 | Sonnenschein ...... A61B 1/0005 600/160 |
| 2004/0122290 | A1 | 6/2004 | Irion et al. |
| 2006/0063976 | A1 | 3/2006 | Aizenfeld et al. |
| 2010/0204546 | A1 | 8/2010 | Hassidov et al. |
| 2010/0245541 | A1* | 9/2010 | Zhao ........................ G01D 1/00 348/45 |
| 2013/0041216 | A1* | 2/2013 | McDowall ............... G02B 5/04 600/109 |
| 2013/0083178 | A1 | 4/2013 | Kotani et al. |
| 2013/0085338 | A1 | 4/2013 | Buerk |
| 2013/0204084 | A1* | 8/2013 | Hale .................. A61B 5/04525 600/109 |
| 2014/0285644 | A1 | 9/2014 | Richardson et al. |
| 2016/0209646 | A1 | 7/2016 | Hattori et al. |
| 2018/0017806 | A1* | 1/2018 | Wang .................. G02B 27/425 |

FOREIGN PATENT DOCUMENTS

| | | |
|---|---|---|
| EP | 2617349 A1 | 7/2013 |
| JP | H09122071 A | 5/1997 |

OTHER PUBLICATIONS

Kobayashi E., et al., "A Wide-Angle View Endoscope System using Wedge Prisms," International Conference on Medical Image Computing and Computer-Assisted Intervention, 2000, vol. 1935, pp. 661-668.

Korniski R., et al., "3D Imaging with a Single-aperture 3-mm Objective Lens: Concept, Fabrication and Test," Proceedings of SPIE, Sep. 2011, vol. 8129, 11 pages.

Leiner D.C., Medical Optics Tutorial—Miniature Optics in the Hospital Operating Room, Dec. 17, 2013, Retrieved from the Internet: URL: https://www.lighthouseoptics.com/endoscope-testing-equipment/medical-optics-tutorial/>, 5 pages.

McGuire J.P., "Manufacturable Mobile Phone Optics: Higher Order Aspheres are not Always Better," Proceedings of SPIE, 2010, vol. 7652, 8 pages.

Peng X., "Design of High Pixel Mobile Phone Camera Lens," Research Journal of Applied Sciences, Engineering and Technology, 2013, vol. 6 (7), pp. 1160-1165.

Roulet P., et al., "360° Endoscopy using Panomorph Lens Technology," Proceedings of SPIE, 2010, vol. 7558, pp. 75580T-1-75580T-13.

Schlegel S., et al., "Chip-on-the-Tip Endoscope with Flexible Tip," Biomedical Engineering, 2012, vol. 57 (Suppl 1), pp. 693.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

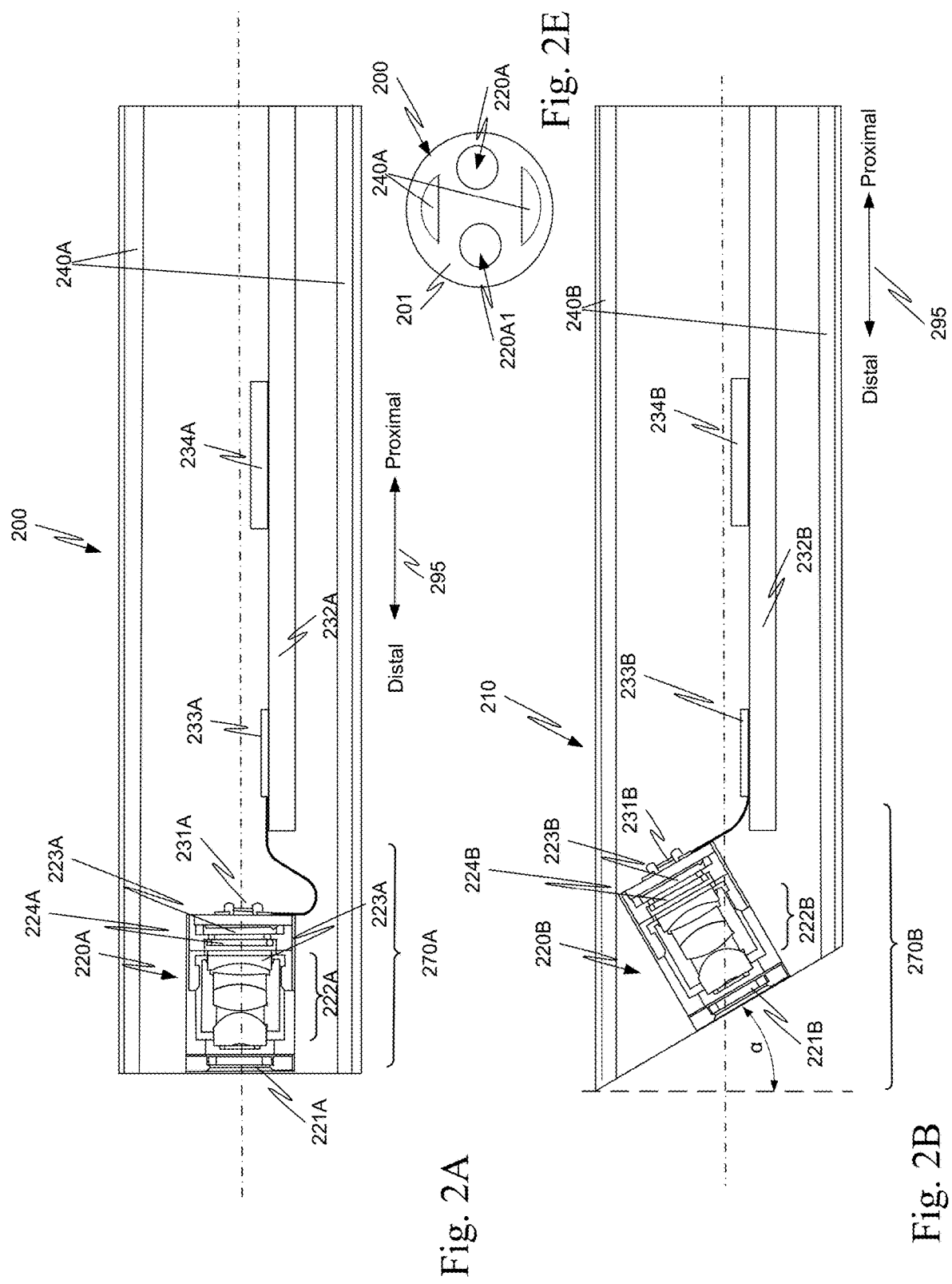

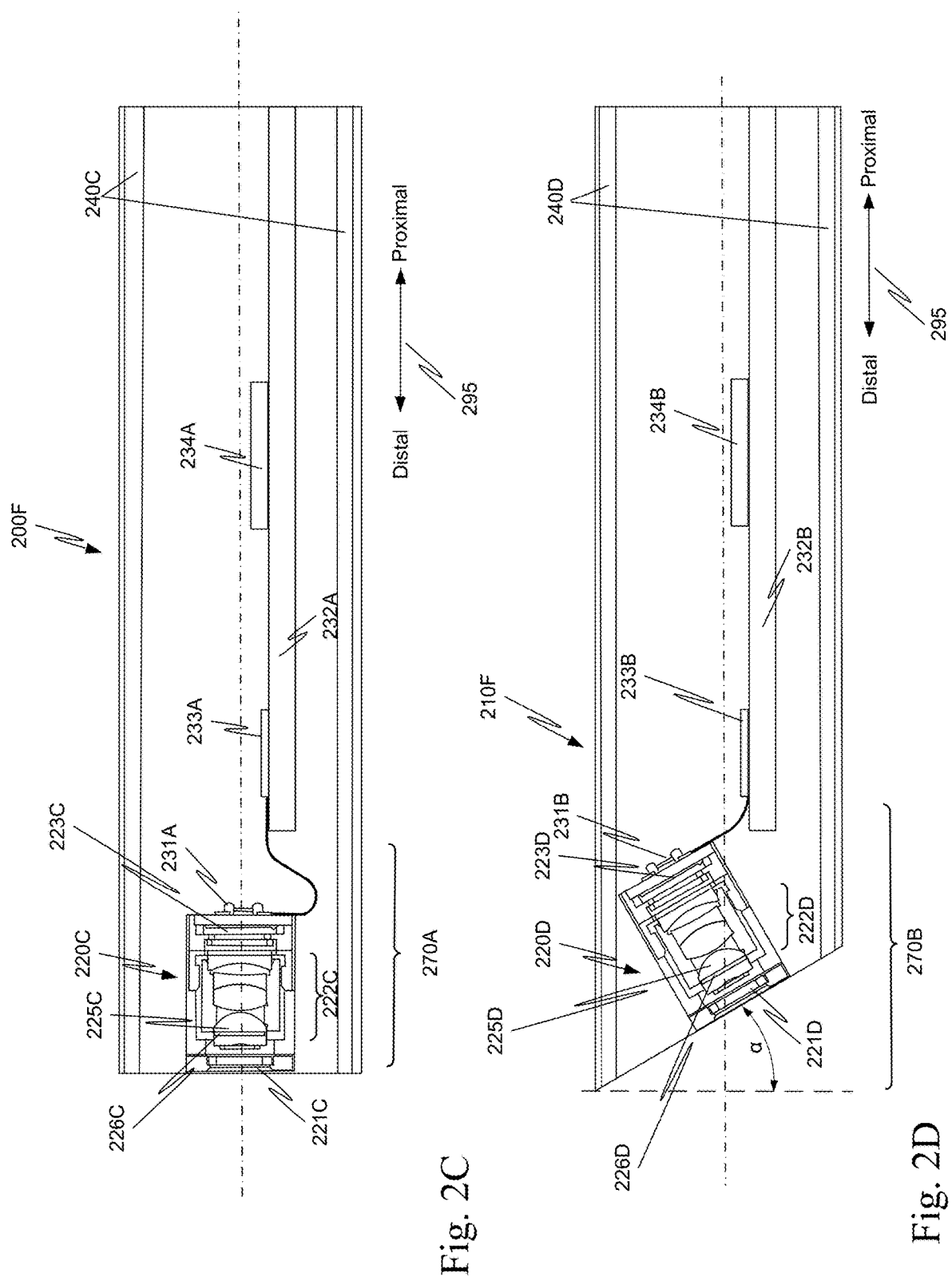

ANGLED ENDOSCOPE TIP IMAGE CAPTURE UNIT

RELATED APPLICATIONS

This application is a continuation of U.S. Ser. No. 15/126,952, filed Sep. 16, 2016, which was the U.S. national phase of International Application No. PCT/US2015/020890, filed Mar. 17, 2015, which designated the U.S. and claims priority to U.S. provisional patent application 61/954,300, filed on Mar. 17, 2014, the contents of each of which are incorporated herein by reference.

BACKGROUND OF THE INVENTION

Field of the Invention

The present invention relates generally to endoscopic image capture units, and more particularly to image capture units mounted in a distal tip of an endoscope.

Description of Related Art

Typically, endoscopes used in minimally invasive surgery come in various tip angles. Two common tip angles are a zero degree angle and a thirty degree angle. A schematic diagram of a portion of an endoscope 100 with a zero degree tip angle is presented in FIG. 1A. An endoscope with a zero degree tip angle is referred to as a zero degree endoscope. A schematic diagram of a portion of an endoscope 110 with a thirty-degree tip angle is presented in FIG. 1B. An endoscope with a non-zero degree tip angle is referred to as a non-zero degree endoscope.

Typically, a stereoscopic endoscope used in minimally invasive surgery includes two optical channels, which are identical in construction. Thus, the portion of the optical channel illustrated in FIGS. 1A and 1B is the same in both channels of a stereoscopic endoscope.

Objective lens system 120 in endoscope 100 includes some of the same lenses as in objective lens system 130, i.e., lens 101A is the same as lens 101B, lens 102A is the same as lens 102B, lens 103A is the same as lens 103B, and lens 104A is the same as lens 104B. However, objective lens system 130 in endoscope 110 also incorporates a prism 131, which directs the line of sight at the desired angle. As used herein, a prism refers to a transparent solid body that refracts light (i.e., changes the direction of light passing through the transparent solid body). As used herein, a substantially flat piece of glass that is not configured to refract light is not a prism.

To facilitate the interchangeability of endoscopes 100 and 110 in a teleoperated surgical system, the optical path length of objective lens system 120 is kept the same as the optical path length of objective lens systems 130. Thus, to compensate for the optical path through prism 131 in objective lens system 130, it is necessary to insert a block of glass 121 in objective lens system 120. The optical path length through block of glass 121 is the same as the optical path length through prism 131.

Thus, each endoscope with a different angled tip requires a different prism. If an endoscope family includes an endoscope with a zero degree tip (FIG. 1A), an endoscope with a thirty-degree tip (FIG. 1B), and an endoscope with a forty-five degree tip (not shown), three different objective lens systems must be manufactured and assembled so that each objective lens system has the same optical path length through the system.

While the optical path lengths of objective lens systems 120 and 130 are the same, light traveling through objective lens system 130 incurs two mirror bounces that light traveling through objective lens system 120 does not incur, i.e., the optical path in objective lens system 130 is folded, while the optical path in objective lens systems 120 is non-folded. The two mirror bounces slightly degrades the image captured using endoscope 110 relative to the image captured using endoscope 100.

Typically, endoscopes 100 and 110 have an outer diameter of 12 mm or 8.5 mm. Consequently, prism 131 is quite small and requires careful, costly, manufacturing.

Also, thirty-degree prism 131 has to be aligned to the other optics precisely. One challenge of this thirty-degree design is that, in a stereoscopic endoscope, the alignment of the right and left eyes requires that the objective lens assemblies in the right and left channels be rotationally aligned so the thirty-degree directions for the right and left channels are pointing in exactly the same direction. While the issues associated with an angled tip endoscope are known, the approach still has been to use an appropriate prism in the endoscope to achieve viewing through the angled tip.

SUMMARY

In one aspect, a teleoperated surgical system includes a non-zero degree endoscope. A non-zero degree endoscope has a distal face that is tilted relative a cylindrical body of a distal portion of that endoscope. In a zero degree endoscope, a distal face is perpendicular to a cylindrical body of a distal portion of that endoscope The non-zero degree endoscope includes a body, a distal portion, and an image capture unit. The distal portion is connected to the body, and the distal portion has a lengthwise axis.

The image capture unit includes a zero degree lens stack. A zero degree lens stack does not include an assembly, such as a prism assembly, to change a view angle of the zero degree lens stack. The zero degree lens stack has a non-folded optical path. The image capture unit also has a lengthwise axis. The image capture unit is mounted in the distal portion of the endoscope with the lengthwise axis of the image capture unit intersecting the lengthwise axis of the body to define a non-zero degree angle. In one aspect, the non-zero degree angle is an acute non-zero degree angle, e.g., a thirty degree angle.

Also, in one aspect, the non-zero degree endoscope is a non-zero degree stereoscopic endoscope including the image capture unit and a second image capture unit. The second image capture unit is substantially identical to the image capture unit.

The two identical image capture units can be implemented in several ways. For example, either each capture unit contains its own respective image capture chip, e.g., image sensor, or there is a single imaging chip, and two regions on the single chip are used as image sensors, one for the first capture unit and another region for the second capture unit. Depending on the suitability and availability of image capture chips with convenient aspect ratios, some implementations may favor one approach or the other. Thus, in some cases, a single imaging chip with a wide aspect ratio is used, e.g., two imaging areas on a single imaging chip may be used with two lens assemblies to capture the stereo image for both eyes or each of the two lens assemblies may have its own imaging chip.

The elimination of the prism or other light folding element in the zero degree lens stack reduces the complexity of manufacture and reduces the complexity of assembly of the non-zero degree endoscope compared with a prior art non-zero degree endoscope that includes a prism block, for example, in the lens stack. Further, since the optical path in the image capture unit of the non-zero degree endoscope is not folded, the image quality is better than the image quality obtained with a prior art non-zero degree endoscope that included a lens stack with a folded optical path.

Further, the elimination of the folded optical paths, e.g., the elimination of the prisms, in the lens systems in a stereoscopic endoscope with a left channel and a right channel makes the alignment of the on-axis image capture units relatively easy—the images in the right and left channels can be aligned and focused independently and the rotation of the zero degree lens systems about the optical axes is not an issue. This is in direct contrast to the prior art non-zero degree stereoscopic endoscope, which has the additional complexity of having to rotationally align the objective lens systems that includes, for example, a thirty degree prism. The alignment of the prior art objective lens systems with prisms is more of a challenge, because, at a minimum, if one objective lens system is even slightly rotated relative to the other, the objective lens systems are not looking in the same direction, and consequently, the stereo image is of very poor quality.

In one aspect, the image capture unit further includes a window positioned proximal to the zero degree lens stack, and an image sensor mounted in the image capture unit proximal to the zero degree lens stack. The image capture unit also includes a stop positioned adjacent to a distal end of the zero degree lens stack.

In another aspect, a teleoperated surgical system includes an endoscope. The endoscope includes a distal portion. The distal portion includes a proximal end, a distal end, and a lengthwise axis extending between the proximal end and the distal end. The endoscope also includes an image capture unit. The image capture unit includes an image forming lens assembly and an image sensor. The image forming lens assembly has a non-folded optical path between an entry location of light into the image forming lens assembly and the image sensor. The image capture unit is mounted at an angle to the lengthwise axis in the distal end of the distal portion of the endoscope.

Again, this endoscope does not include a prism assembly or other light folding element in the image forming lens assembly to change a view angle of the image forming lens assembly. Thus, this endoscope has the same advantages over the prior art non-zero degree endoscope, as described above.

In one aspect, the endoscope is a stereoscopic endoscope including the image capture unit and a second image capture unit. The second image capture unit is substantially identical to the image capture unit.

The image capture unit of this endoscope also includes a window positioned proximal to the image forming lens assembly, and a stop positioned adjacent to a distal end of the image forming lens assembly. In one aspect, a distal lens of the image forming lens assembly includes a filter embedded in the lens, e.g., the distal lens comprises a sandwich lens.

A family of endoscopes for a teleoperated surgical system includes a non-zero degree endoscope and a zero degree endoscope. The zero degree endoscope includes a first distal portion and a first image capture unit. The first distal portion has a first lengthwise axis. The first image capture unit has a second lengthwise axis. The first image capture unit is mounted in the first distal portion with the second lengthwise axis of the first image capture unit substantially parallel to the first lengthwise axis of the first distal portion. As used herein, substantially parallel means parallel to within manufacturing and assembly tolerances.

The non-zero degree endoscope of the family includes a second distal portion and a second image capture unit. The second distal portion has a third lengthwise axis. The second image capture unit has a fourth lengthwise axis. The second image capture unit is mounted in second distal portion of the non-zero degree endoscope with the fourth lengthwise axis of the second image capture unit intersecting the third lengthwise axis at a non-zero angle.

Each of the first and second image capture units in the family have nearly identical non-folded optical paths between an entry location of light into each image capture unit and an imager of each image capture unit. In one aspect, the zero degree endoscope and the non-zero degree endoscope of the family are both stereoscopic endoscopes. Herein, nearly identical non-folded optical paths and substantially identical non-folded optical paths means that the optical paths are equal to within manufacturing and assembly tolerances.

A method of making the family of endoscopes includes mounting a first image capture unit in a zero degree endoscope. The first image capture unit includes a first optical structure positioned between a window of the first image capture unit and an imager of the first image capture unit. The method also includes mounting a second image capture unit in a non-zero degree endoscope. The second image capture unit includes a second optical structure positioned between a window of the second image capture unit and an imager of the second image capture unit. The first optical structure and the second optical structure are substantially identical and have a non-folded optical path.

A method of manufacturing each of the endoscopes in the family of endoscopes includes mounting an image capture unit in a body of the endoscope by moving the image capture unit through an opening in a distal face of the body. A camera retainer is then mounted in the opening of the distal face to maintain the image capture unit within the body.

BRIEF DESCRIPTION OF THE DRAWINGS

FIG. 2A is an illustration of one aspect of a distal body portion of a zero degree endoscope.

FIG. 2B is an illustration of one aspect of a distal body portion of a non-zero degree endoscope.

FIG. 2C is an illustration of one aspect of a distal body portion of a zero degree endoscope that includes a filter embedded in a distal lens of an image forming lens assembly.

FIG. 2D is an illustration of one aspect of a distal body portion of a non-zero degree endoscope that includes a filter embedded in a distal lens of an image forming lens assembly.

FIG. 2E is an illustration of the distal face of the body portion of FIG. 2A.

Figure 1A:
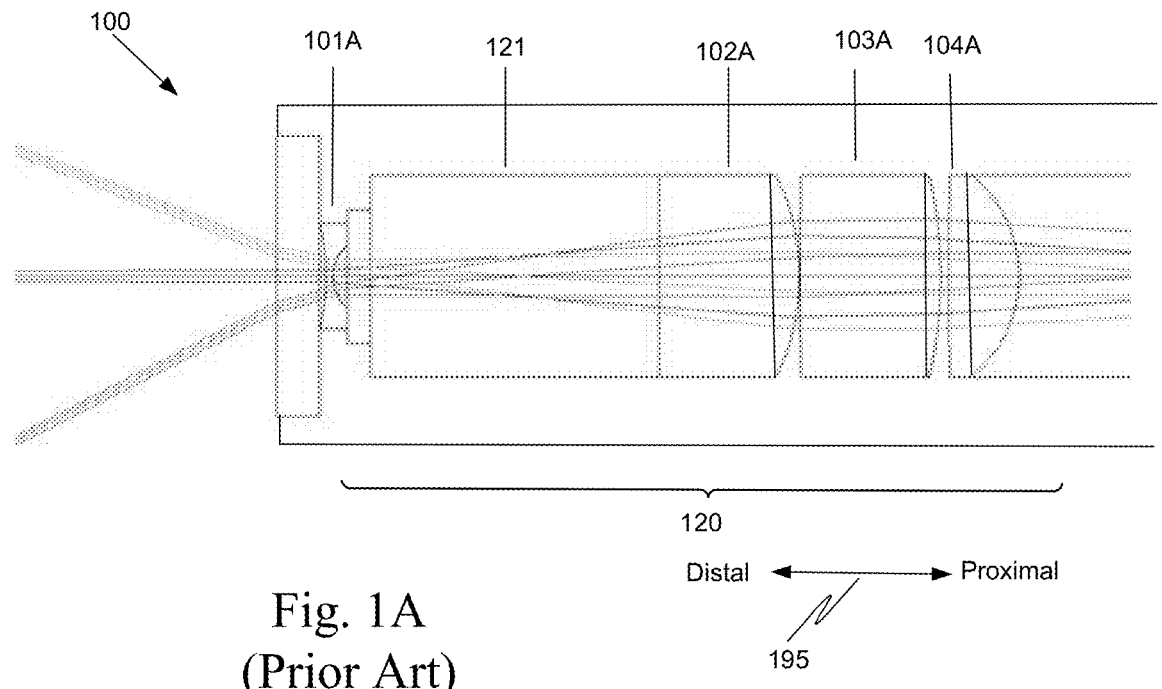
FIG. 1A is an illustration of a prior-art zero degree endoscope.
Figure 1B:
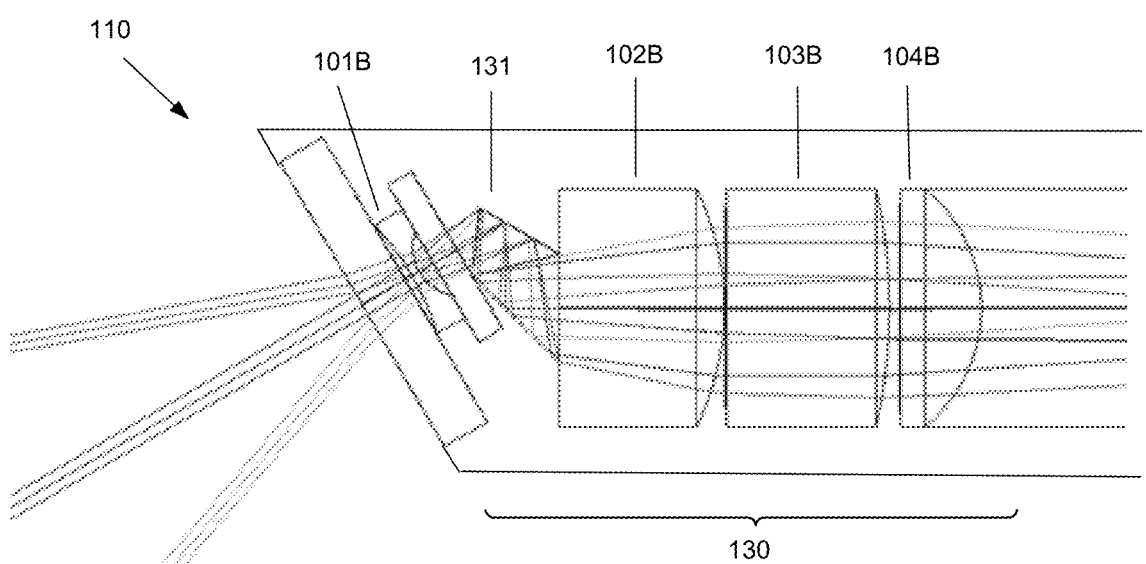
FIG. 1B is an illustration of a prior-art non-zero degree endoscope.

In the drawings, the first digit of a reference number indicates the figure in which the element with that reference number first appeared.

DETAILED DESCRIPTION

In one aspect, a zero degree endoscope 200 (FIG. 2A) and a non-zero degree endoscope 210 (FIG. 2B) use a same image capture unit 220A, 220B. Specifically, image capture units 220A, 220B, sometimes referred to as cameras, are identical to within manufacturing and assembly tolerances, i.e., are substantially identical.

FIGS. 2A and 2B illustrate only the parts of the endoscopes needed to understand the inventive aspects described herein. Also, rather than repeat a sentence for each of the zero degree endoscope 200 and non-zero degree endoscope 210, when the description is applicable to elements in both of these endoscopes, the reference numbers of the elements separated by a comma are used in the description.

Each of image capture units 220A, 220B is mounted in a distal portion 270A, 270B of the endoscope. Each of image captures units 220A, 220B includes a same window 221A, 221B, a same objective lens system 222A, 222B, and a same image sensor 223A, 223B. Sometimes objective lens system 222A, 222B is referred to as an image forming lens assembly. Each of the endoscopes also includes illumination light channels 240A, 240B, which may be implemented either as glass fibers, plastic fibers, or light pipes from a remote source or a light emitting diode or other light emitting device, and which are located as shown.

As used here, "same" does not mean shared. Rather, "same" means that image capture unit 220A is indistinguishable from image capture unit 220B in that the same number, size, and configuration of components are used in each of image capture units 220A and 220B.

Each of image capture units 220A, 220B can include one or more filters to process light that is captured by each of image sensors 223A, 223B (see FIGS. 2C and 2D). Also, each of image capture units 220A, 220B can optionally include a color filter array, such as a Bayer pattern color filter array as part of image sensor 223A, 223B. Image sensor 223A, 223B includes a cover window 224A, 224B in the distal face of image sensor 223A, 223B. This permits manufacture of image sensor 223A, 223B in a separate facility from where image sensor 223A, 223B is assembled with objective lens system 222A, 222B, because cover window 224A, 224B prevents any debris from entering image sensor 223A, 223B. In one aspect, each of image capture units 220A, 220B includes a stop proximal to window 221A, 221B and distal to and adjacent to a distal end of objective lens system 222A, 222B.

For example, each of the image sensor in a stereoscopic endoscope can be either separate image capture chips, or two regions on a single image capture chip. Depending on the suitability and availability of image capture chips with convenient aspect ratios, some implementations may favor one approach or the other. Thus, in some cases, a single imaging chip with a wide aspect ratio is used, e.g., two imaging areas on a single imaging chip may be used with two lens assemblies to capture the stereo image for both eyes or each of the two lens assemblies may have its own imaging chip.

In both zero degree endoscope 200 and in non-zero degree endoscope 210, each of objective lens systems 222A, 222B is a zero degree lens stack. A zero degree lens stack is a lens stack that does not include a light folding assembly, such as the prior art prism assembly, to change an angle of the field of view of the lens stack. Stated another way, the optical path through a zero degree lens stack is a non-folded optical path.

The zero degree lens stacks in zero degree endoscope 200 and non-zero degree endoscope 210 are substantially identical. Substantially identical means that the zero degree lens stacks are identical except for differences associated with manufacturing and assembly tolerances. The zero degree lens stack is a short lens stack compared to a lens stack commonly mounted in a distal end of a conventional endoscope, such as endoscopes 100 and 110.

Prism 131 in objective lens system 130 of prior art thirty-degree endoscope 110 has been eliminated in the non-zero degree endoscopes of this invention. Thus, a single image capture unit can be manufactured and used in both zero degree and non-zero degree endoscopes 200, 210. Not only has the manufacturing been simplified, but also the elimination of the prism in the objective lens system of a non-zero degree endoscope reduces the cost of manufacture.

In addition, the elimination of light folding elements in the objective lens system in a non-zero degree stereoscopic endoscope with a left channel and a right channel makes the alignment of the on-axis image capture units relatively easy—the images in the right and left channels can be aligned and focused independently. The rotation of the objective lens systems about the optical axes is not an issue. This is in direct contrast to the prior art non-zero degree stereoscopic endoscope 110, which has the additional substantial complexity of having to align the objective lens systems that includes, for example, a thirty degree prism.

The alignment of the prior art objective lens systems with prisms is more of a challenge, because, at a minimum, if one objective lens system is rotated relative to the other, the objective lens systems are not looking in the same direction. Image capture unit 220B completely eliminates this problem, because a prism is not needed in the objective lens system of image capture unit 220B.

Both image capture unit 220A and image capture unit 220B have the same non-folded optical path length. Thus, unlike prior art endoscopes 100 and 110, the image captured by non-zero degree endoscope 210 is not degraded relative to the image captured by zero degree endoscope 200.

In both zero degree endoscope 200 and non-zero degree endoscope 210, image capture units 220A, 220B, respectively, are placed into distal portion 270A, 270B of the endoscope from the distal end (from the front of the endoscope) and then held in place by a single part, sometimes referred to as a camera retainer, that is welded in place, in one aspect. The distal and proximal directions in FIGS. 2A and 2B are indicated by arrow 295.

In one aspect, image capture unit 220A, 220B is coupled to a printed circuit board interface 231A, 231B. Printed circuit board interface 231A, 231B in turn is coupled to a printed circuit board 232A, 232B by a flexible circuit. Analog to digital integrated circuit 233A, 233B and transmission integrated circuit 234A, 234B are mounted on printed circuit board 232A, 232B. Analog to digital integrated circuit 233A, 233B is coupled to image capture unit 220A, 220B and is coupled to a transmission integrated circuit 234A, 234B. Transmission integrated circuit 234A, 234B converts the electric digital signals to optical signals for transmission over a fiber optic cable.

Endoscope 200F (FIG. 2C) is the same as endoscope 200 (FIG. 2A) except image capture unit 220C replaces image capture unit 220A. Endoscope 210F (FIG. 2D) is the same as endoscope 210 (FIG. 2B) except image capture unit 220D replaces image capture unit 220B. Image capture units 220C, 220D, sometimes referred to as cameras, are identical to within manufacturing and assembly tolerances. FIGS. 2C and 2D illustrate only a distal part of the body of the endoscopes needed to understand the inventive aspects described herein.

Each of image captures units 220C, 220C includes a same window 221C, 221D, a same objective lens system 222C, 222D, a same image sensor 223C, 223D. Sometimes objective lens system 222C, 222D is referred to as an image forming lens assembly. Window 221C, 221D is the same as window 221A, 221B. Image sensor 223C, 223D is the same as image sensor 223A, 223B. Light channels 240C, 240D are the same as light channels 240A, 240B.

However, in this aspect, objective lens system 222C, 222D includes a filter 226C, 226D embedded within, e.g., sandwiched within, a lens 225C, 225D of objective lens system 222C, 222D. In one aspect, filter 226C, 226D filters out fluorescence excitation illumination light. Filter 226C, 226D is placed in objective lens system 222C, 222D at a location where the light rays are most perpendicular to filter 226C, 226D, e.g., within most distal lens 225C, 225D. For example, lens 225C, 225D is sliced into two pieces and filter 226C, 226D inserted between the two pieces and then the pieces are bonded together to form a hamburger in a bun like lens and filter assembly.

The advantage of placing filter 226C, 226D, e.g., a fluorescence notch filter, at this position in the lens assembly is that as objective lens system 222C. 222D is made short, the ray angles at image sensor 223C, 223D increase thus making the placement of filter 226C, 226C on the cover glass of image sensor 223C, 223D less advantageous. The ray angles may be made shallower (even accounting for the index of the medium in which the rays travel) at a surface internal to one of the lens components in objective lens system 222C, 222D and that is where filters 226C, 226D are placed in this aspect.

In this system, filter 226C, 226D is placed internal to first lens 225C, 225D in a unique hamburger like construction which also affords the possibility of making filter 226C, 226D oversized, cementing filter 226C, 226D between the pieces of lens 225C, 225D, and then edging the assembly down thereby protecting the filter surface and guaranteeing that the filter will perform well to the very edge of the lens. Positioning filter 226C, 226D near the front, i.e., near the distal end, of objective lens system 222C, 222D also provides the best protection from stray fluorescence illumination from entering the rest of the lens system, which is advantageous as stray fluorescence illumination is undesirable and hurts image contrast. The position internal to lens 225C, 225D is better than placing filter 226C, 226D at the stop because the ray angles can be designed to intersect filter 226C, 226D at a shallower angle.

FIG. 2E is a view of a distal face 201 of zero degree endoscope 200. Distal face 201 includes openings for each of image capture units 220A and 220A1 and for each of light channels 240A. Image capture units 220A and 220A1 are substantially identical. The distal faces of the other endoscopes in FIGS. 2B, 2C, and 2D include the same elements as distal face 201, and so the distal face is not illustrated for each aspect.

Figure 3:
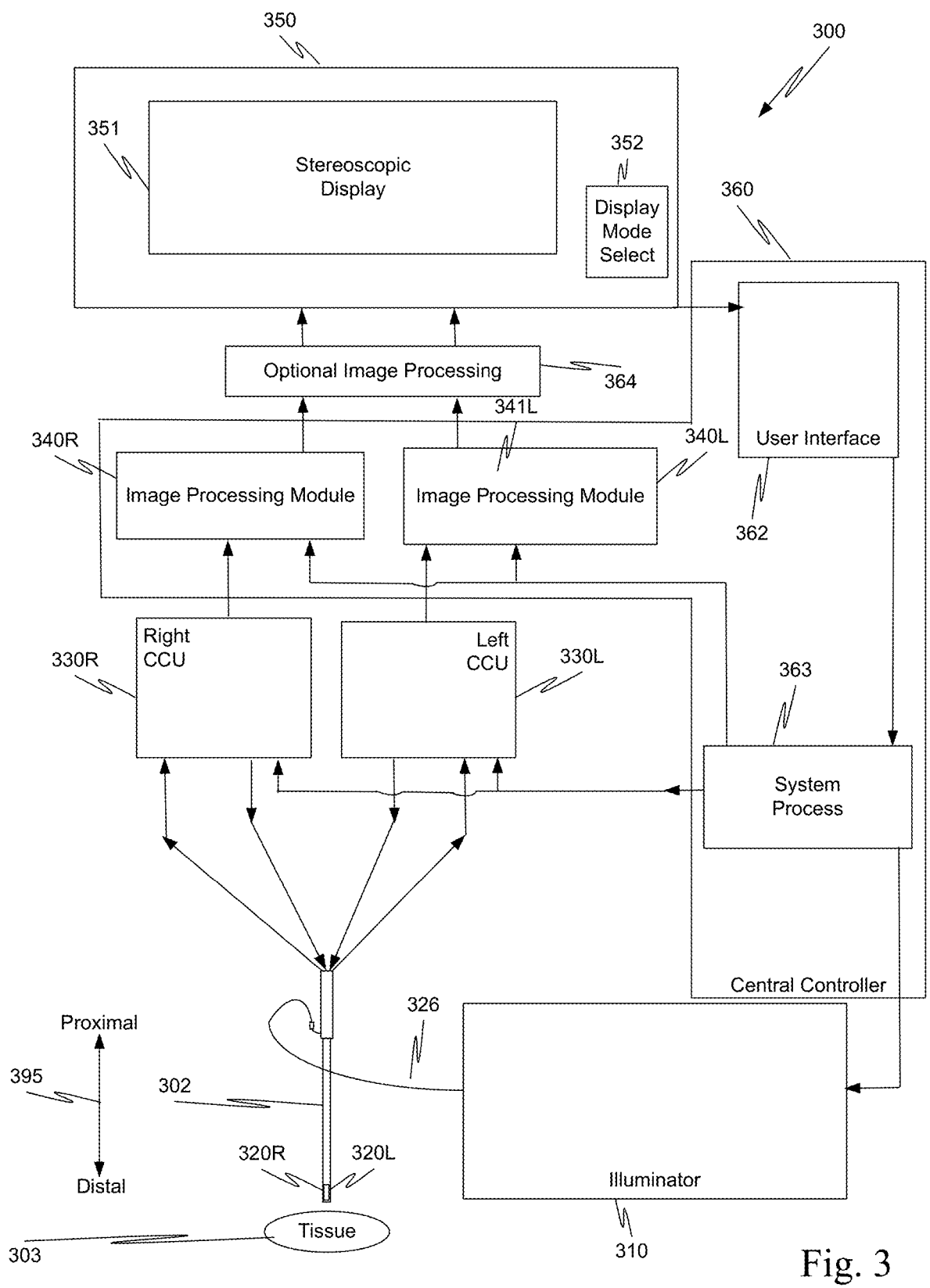
FIG. 3 is an illustration of a teleoperated surgical system that includes a stereoscopic endoscope that can be either of a stereoscopic zero degree endoscope and a stereoscopic non-zero degree endoscope.

Aspects of this invention facilitate acquiring stereoscopic images of a scene in a surgical field. Referring to FIG. 3, for example, image capture units 320L, 320R (FIG. 3) are located at a distal end of a stereoscopic endoscope 302 in a teleoperated surgical system 300, e.g., a da Vinci®. minimally invasive teleoperated surgical system commercialized by Intuitive Surgical, Inc. of Sunnyvale, Calif. As indicated by arrow 395, the distal direction is towards tissue 303 and the proximal direction is away from tissue 303.

One image capture unit 320L captures left side images for a stereoscopic image, sometimes referred to as left side stereoscopic images. A second image capture unit 320R captures right side images for a stereoscopic image, sometimes referred to as right side stereoscopic images. Herein, use of a stereoscopic endoscope is illustrative only, and is not intended to be limiting. In view of the disclosure, an endoscope with a single image capture unit configured to capture light from tissue 303, e.g., a monoscopic endoscope, could be used. This endoscope would have only one of the two optical channels described herein for the stereoscopic endoscope.

Figure 5A:
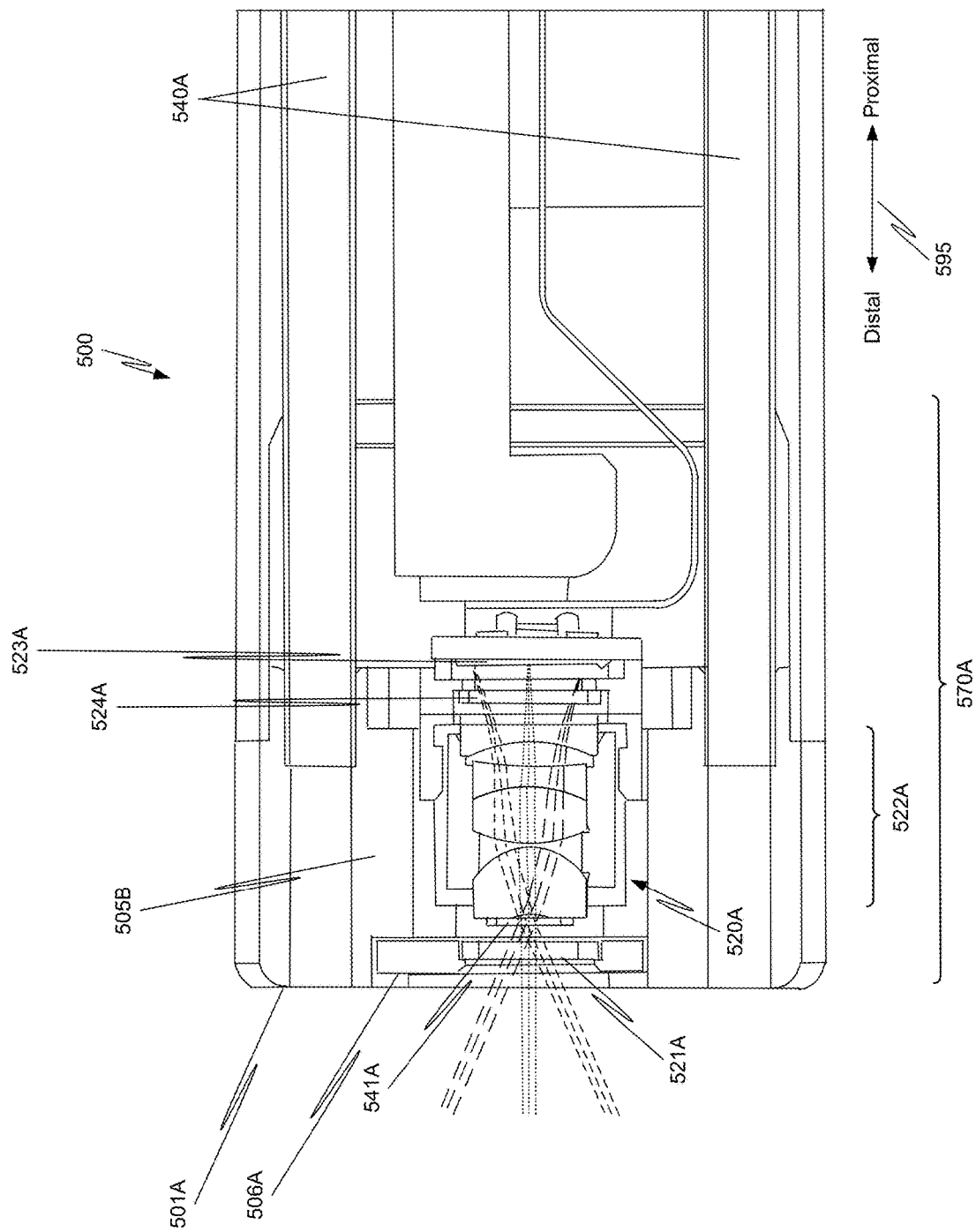
FIG. 5A is an enlarged illustration of the distal body portion of the zero degree endoscope of FIG. 2A.
Figure 5B:
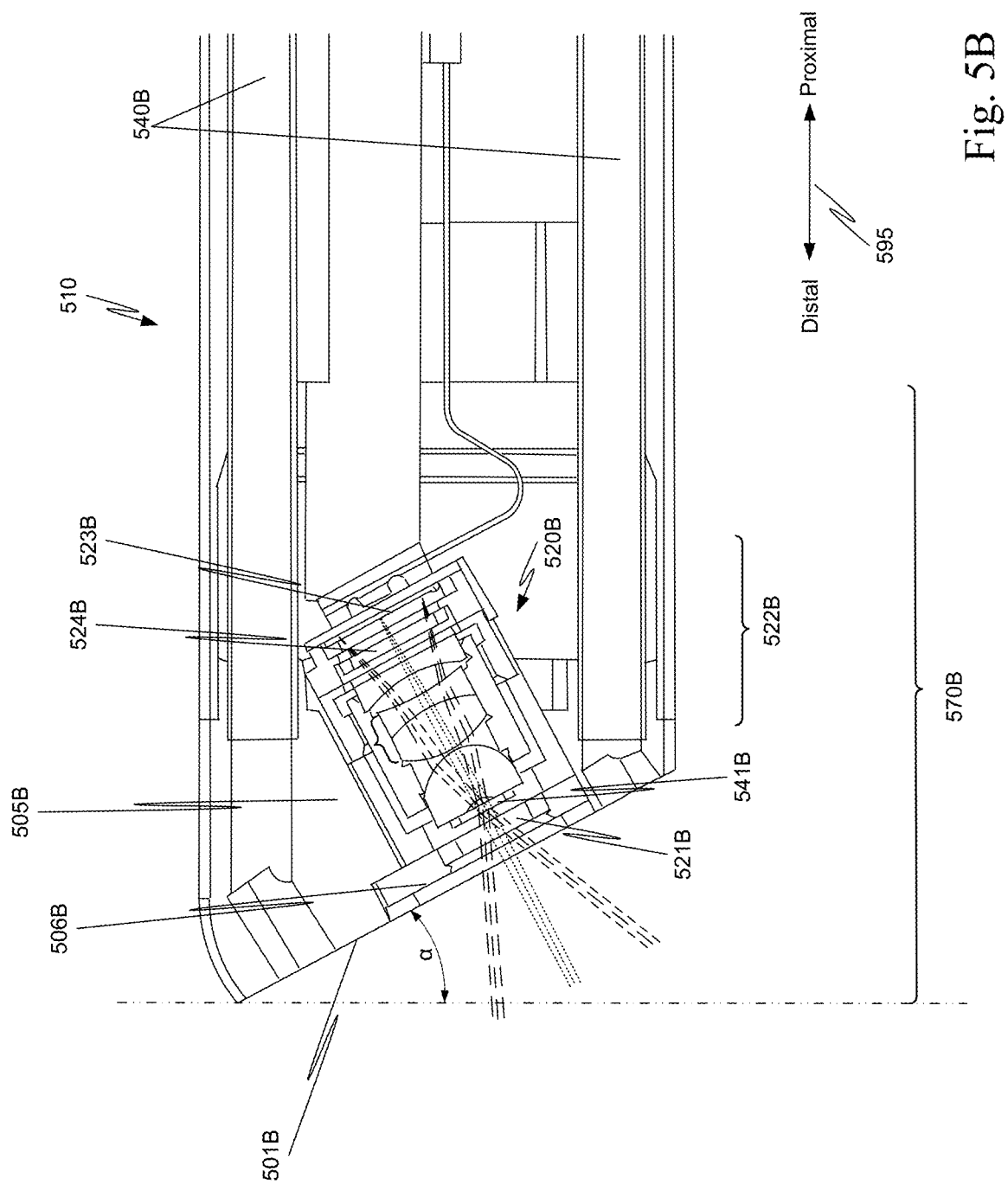
FIG. 5B is an enlarged illustration of the distal body portion of the non-zero degree endoscope of FIG. 2B.

As described above and as described more completely below, each image capture unit 320L, 320R includes an image forming lens assembly and a sensor assembly. The image forming lens assembly is the same irrespective of whether stereoscopic endoscope 302 is a zero degree stereoscopic endoscope or a non-zero degree stereoscopic endoscope. One example of the image capture units and the image forming lens assembly are shown in FIGS. 5A and 5B. As indicated previously, the image forming lens assembly in each of the image capture units has the same non-folded optical path.

In this example, a surgeon at surgeon's console 350 remotely manipulates endoscope 302 that is mounted on a robotic manipulator arm (not shown). There are other parts, cables, etc. associated with the da Vinci® Surgical System, but these are not illustrated in FIG. 3 to avoid detracting from the disclosure. Further information regarding minimally invasive surgical systems may be found for example in U.S. patent application Ser. No. 11/762,165 (filed Jun. 23, 2007; disclosing Minimally Invasive Surgical System), U.S. Pat. No. 6,837,883 B2 (filed Oct. 5, 2001; disclosing Arm Cart for Telerobotic Surgical System), and U.S. Pat. No. 6,331,181 (filed Dec. 28, 2001; disclosing Surgical Robotic Tools, Data Architecture, and Use), all of which are incorporated herein by reference.

An illuminator 310 is coupled to stereoscopic endoscope 302. Illuminator 310 includes at least a white light source and optionally may include one or more fluorescence excitation sources. Illuminator 310 is used in conjunction with at least one illumination channel in stereoscopic endoscope 302 to illuminate tissue 303. Alternatively and without loss of generality, illuminator 310 may be replaced by an illumination source at the distal tip, or near the distal tip, of endoscope 302. Such distal tip illumination may be provided by LEDs, for example, or other illumination sources.

In one example, illuminator 310 provides white light illumination that illuminates tissue 303 in white light. In some implementations, illuminator 310 can also provide non-visible light that excites fluorescence and/or a subset of the visible color components that make-up white light.

Light from illuminator 310 is directed onto an illumination channel 326 that couples illuminator 310 to the illumination channel in endoscope 302. The illumination channel in stereoscopic endoscope 302 directs the light to tissue 303. In another, aspect, an illumination source, such as LEDs or other sources, is provided at, or near the distal tip on endoscope 302. The illumination channels can be implemented with a fiber optic bundle, a single stiff or flexible rod, or an optical fiber.

Image capture unit 320L is coupled to a stereoscopic display 351 in surgeon's console 350 via a left camera control unit (CCU) 330L. Image capture unit 320R is coupled to stereoscopic display 351 in surgeon's console 350 via a right camera control unit (CCU) 330R. Camera control units 330L, 330R receive signals from a system process module 363 that controls gains, controls capturing images, controls transferring captures images to dual image enhancement modules 340R, 340L, etc. System process module 363 represents the various controllers including the vision system controllers in system 300. Camera control units 330L, 330R may be separate units, or may be combined in a single dual controller unit.

Display mode select switch 352 provides a signal to a user interface 362 that in turn passes the selected display mode to system process module 363. Various vision system controllers within system process module 363 configure illuminator 310 to produce the desired illumination, configure left and right camera control units 330L and 330R to acquire the desired images, and configure any other elements needed to process the acquired images so that the surgeon is presented the requested images in display 351.

Imaging processing modules 340R, 340L, in one aspect, transform the color of the acquired images to a new desired color balance as determined by system process module 363. As shown in FIG. 3, user interface 362, system process module 363, and image processing modules 340L, 340R are grouped as a central controller 360 for descriptive purposes. Optional image processing module 364 receives video from central controller 360 and processes images from image processing modules 341L and 341R prior to display on stereoscopic display 351 in surgeons console 350. Optional image processing module 364 is equivalent to image processing modules in prior art minimally invasive surgical systems and so is not considered in further detail.

Although described as central controller 360, it is to be appreciated that central controller 360 may be implemented in practice by any number of modules and each module may include any combination of components. Each module and each component may include hardware, software that is executed on a processor, and firmware, or any combination of the three. Also, the functions and acts of central controller 360, as described herein, may be performed by one module, or divided up among different modules or even among different components of a module. When divided up among different modules or components, the modules or components may be centralized in one location or distributed across system 300 for distributed processing purposes. Thus, central controller 360 should not be interpreted as requiring a single physical entity, as in some aspects central controller 360 is distributed across system 300.

Figure 4A:
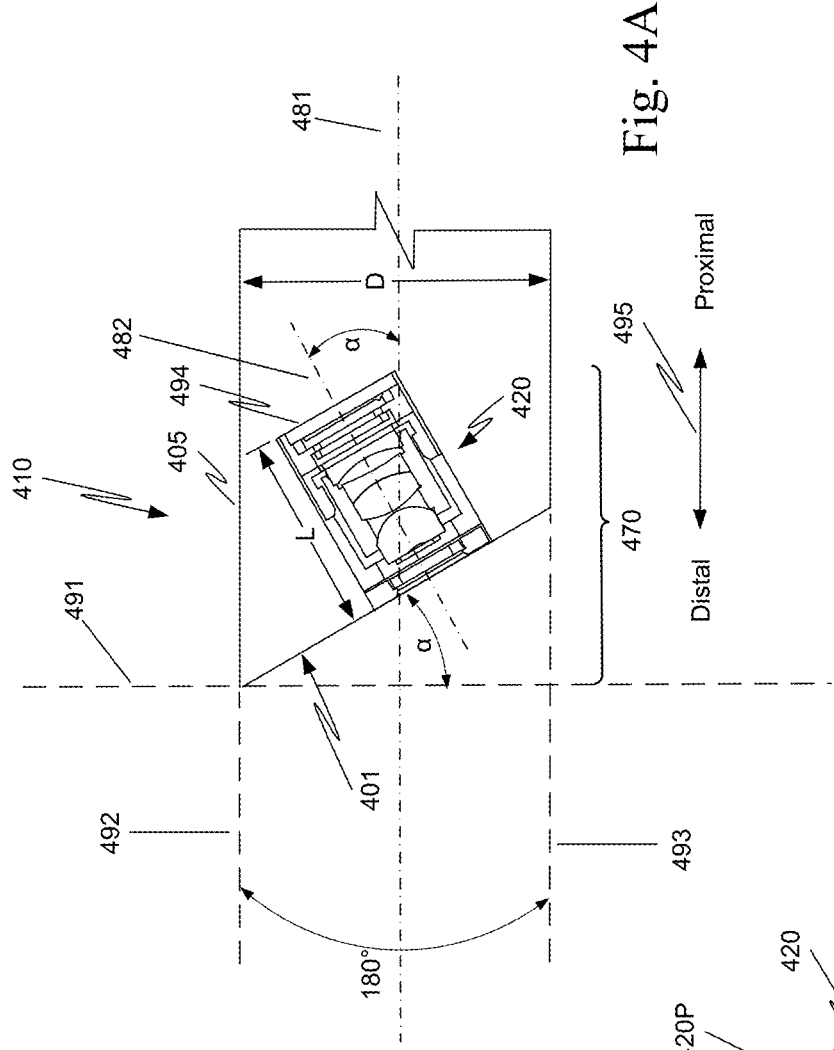
FIGS. 4A and 4B are illustrations used to explain the angle of an image capture unit in a non-zero degree endoscope.
Figure 4B:
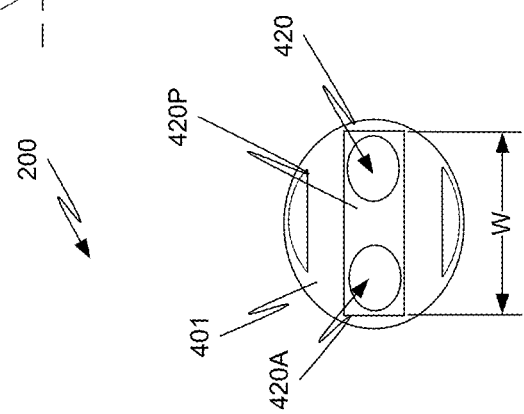

As used herein, a non-zero degree endoscope 410 (FIG. 4A), sometimes referred to as endoscope 410, is an endoscope with an inner diameter D and a distal face 401 oriented at a non-zero angle α with respect to a vertical plane 491. FIG. 4B is a schematic illustration of distal face 401 of endoscope 410 with the camera retainer removed. FIG. 4B shows that image capture unit package 420P includes two image capture units 420 and 420A that are substantially identical. Image capture unit package 420P has a width W, which extends into and out of the page in FIG. 4A. The distal and proximal directions in FIG. 4 are indicated by arrow 495. If angle α is zero degrees, zero degree endoscope 200 (FIG. 2A) is obtained.

As used here, a vertical plane 491 is perpendicular to two planes 492, 493 tangent to the outer side surface of body 405 of distal portion 470 of endoscope 410 and is perpendicular to a lengthwise axis 481 of endoscope 410. The lines in planes 492, 493 that are tangent to the outer side surface are separated by one hundred-eighty degrees. Thus, distal face 401 is tilted at an angle with respect to body 405 of distal portion 470 of endoscope 410. In a zero degree endoscope, angle α is zero degrees, and so distal face 401 would be perpendicular to body 405. See zero degree endoscope 200 (FIG. 2A).

Alternatively, angle α can be defined with respect to a lengthwise axis 481 of distal portion 470 of endoscope 410. Angle α is defined by the intersection of a lengthwise axis 482 of image capture unit 420 with lengthwise axis 481. Stated another way, angle α is an acute non-zero angle formed by the intersection of lengthwise axis 482 of image capture unit 420 with lengthwise axis 481 of distal portion 470 of non-zero degree endoscope 410.

Angle α can vary from zero degrees to some maximum angle $α_{max}$. Angle α is limited to some maximum angle $α_{max}$ by the cross sectional area and shape of image capture package 420P in tube body 405. As camera 420 is tilted, image capture package 420P may intersect tube body 405, and thus limit angle α. Hence, for a given inner diameter D of endoscope 410, angle α can only be increased only until an edge or a corner of a proximal face 494 of image capture unit 420 contacts the inner cylindrical surface of tube body 405.

In the example of FIG. 4A, capture package 420P has a length L, which is also the length of each image capture unit 420, 420A, and a width W. Distal portion 470 of tube body 405 has inner diameter D. In one aspect, for an angle α of thirty degrees and an outer diameter of 12 mm, length L is 5.9 mm.

FIGS. 5A and 5B are an enlarged illustrations of a window 521A and image capture unit 520A of a zero degree endoscope 500 mounted in a distal portion 570A of zero degree endoscope 500 and a window 521B and image capture unit 520B mounted in a distal portion 570B of a non-zero degree endoscope 510, respectively. As indicated above, image capture units 520A, 520B are substantially identical except for the angle at which image capture units 520A, 520B are mounted in the distal portions of their respective endoscopes. The distal and proximal directions in FIGS. 5A and 5B are indicated by arrow 595.

Thus, in the following description the components of image capture unit 520B are considered. However, this description is directly applicable to the components of image capture unit 520A with the "B" in the reference numeral replaced with an "A," and so the description is not repeated for the components in image capture unit 520A.

In one aspect, window 521B is a sapphire window. The use of sapphire windows is known and sapphire window 521B has characteristics equivalent to those typically found in windows of other teleoperated endoscopes. Window 521B separates the components in image capture unit 520B from the environment external to endoscope 510.

In the aspect of FIG. 5B, the number and configuration of lenses in objective lens system 522B is limited by the length L of image capture unit 520B (see FIG. 4A). Once a length L is selected, as described with respect to FIG. 4A, the lens stack is designed and manufactured in a conventional manner.

Stop 541B is a fixed size stop and the exposure of image capture unit 520B is fixed. The other features of endoscope 510 are the same as those described above, e.g., illumination channels 540B are the same as illumination channels 240B, and image sensor 523B and cover window 524B are the same as image sensor 223B and cover window 224B, respectively.

FIGS. 5A and 5B illustrate endoscopes in a family of endoscopes, where the optical paths in the family are substantially identical. This is achieved, as described previously, by using substantially identical image capture units in each of the endoscopes in the family Again, "substantially identical" as used herein means identical to within manufacturing and assembly tolerances.

As explained more completely below, each endoscope in the family of endoscopes includes in the assembly of the endoscope, mechanically mounting an image capture unit 520A, 520B in a body 505A, 505B of an endoscope 500, 510 by moving image capture unit 520A, 520B through an opening in a distal face 501A, 501B of body 505A, 505B. A camera retainer 506A, 506B is mounted in the opening of distal face 501A, 501B to hold image capture unit 520A, 520B with window 521A, 521B in place.

Figure 6A:
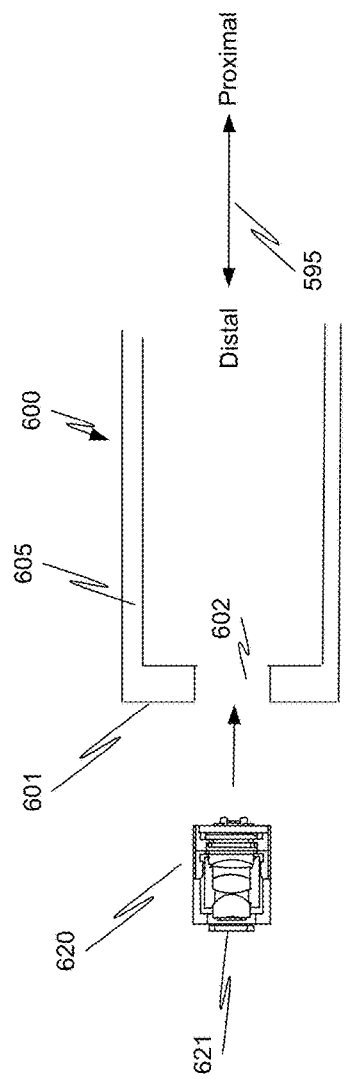
FIGS. 6A to 6C illustrates aspects in the manufacture of the endoscopes illustrated in FIGS. 2A to 2D, 3, 5A, and 5B.
Figure 6B:
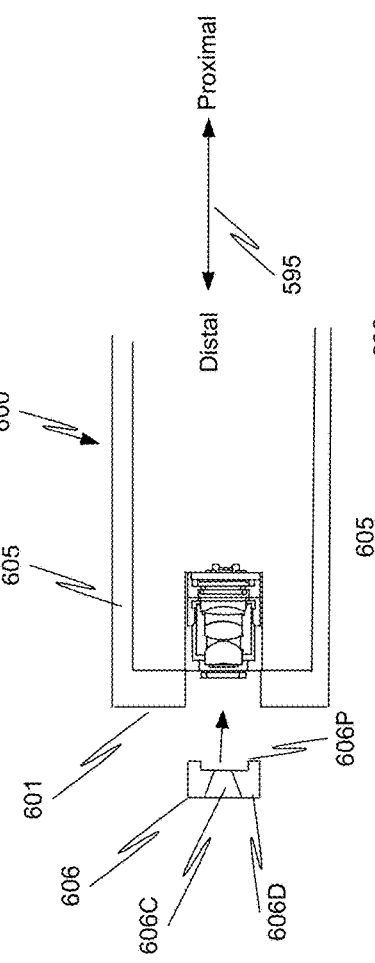
Figure 6C:
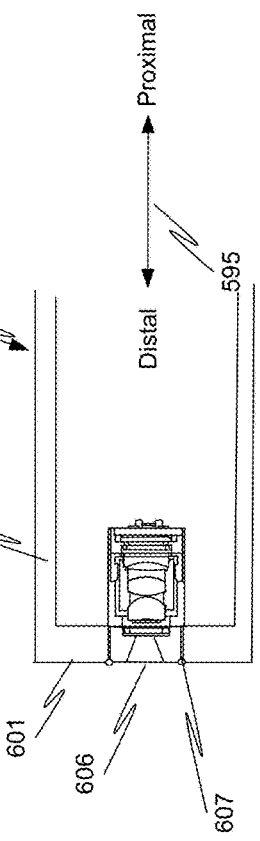

FIGS. 6A to 6C are schematic illustrations of one aspect of manufacturing the endoscopes described with respect to FIGS. 2A to 2D, 3, 5A, and 5B. The manufacturing process is the same for a monoscopic endoscope and a stereoscopic endoscope, and so the description is not repeated for both types of endoscopes.

While a zero degree endoscope 600 is used in the example, the procedure is identical for a non-zero degree endoscope, when the sloped distal face is taken into consideration. Also, in FIGS. 6A to 6C many of the details of the endoscopes are not illustrated, because the details are not necessary to understand this aspect of the manufacturing process. The distal and proximal directions in FIGS. 6A to 6C are indicated by arrow 695.

Image capture unit 620 can be part of an image capture unit package. Also, image capture unit 620 is identical to within manufacturing and assembly tolerances to the image capture units illustrated and described with respect to FIGS. 2A to 2E, 3, 4A 4B, 5A, and 5B. Thus, the details of image capture unit 620 are not repeated here.

Initially, image capture unit 620 is positioned distal to a distal face 601 of body tube 605 of endoscope 600 and is moved in a proximal direction towards an opening 602 in distal face 601. (FIG. 6A) Image capture unit 620 is passed through opening 602 and is mechanically mounted within body tube 605. (See FIGS. 5A and 5B.)

Finally, a camera retainer 606 is positioned distal to distal face 601 of body tube 605 of endoscope 600 and is moved in a proximal direction towards opening 602. Camera retainer 606 is positioned in opening 602 so a proximal face 606P of camera retainer 606, sometime referred to as an inner face or a first surface, contacts image capture unit 620 and a distal face 606D of camera retainer 606, sometimes referred to as an outer face or a second surface, is aligned with distal face 601, e.g., distal face 606D is in a same plane as distal face 601. Camera retainer 606 is secured to body tube 606 so that camera unit 620 is held in place. In one aspect, when body tube 605 and camera retainer 606 are both made of metal, a weld 607 is used to secure body tube 605 to camera retainer 606.

As shown in FIGS. 6B and 6C, a channel 606C extends through camera retainer 606 from distal face 606D to a proximal face 606P, or stated alternatively, a channel extends through a camera retainer from a first surface to a second surface where the first surface is opposite and removed from the second surface. The size of the opening of channel 606C in proximal face 606P is smaller than the size of window 621 of camera unit 620 so that window 621 on the distal face of camera unit 620 is retained in place.

In some of the above description and in some of the drawings a single image capture unit has been used. As in known to those knowledgeable in the field, a stereoscopic endoscope includes an image capture unit in the left channel and an image capture unit in the right channel. Both of these image capture units have the same characteristics, features, etc. as described for the single image capture unit and so repeating the description and drawings for both channels in a stereoscopic endoscope provides no additional information. Thus, to avoid duplication and detracting from the description of the inventive aspects, only one of the two image capture units in a stereoscopic endoscope was described in some aspects. Moreover, as described above, the novel image capture units in a non-zero degree stereoscopic endoscope have many advantages over a prior art non-zero degree stereoscopic endoscope that included a non-zero degree prism in the optical path so that the optical path was folded.

Herein, all examples and illustrative references are non-limiting and should not be used to limit the claims to specific implementations and embodiments described herein and their equivalents. In view of this disclosure, particular features described in relation to one aspect or embodiment may be applied to other disclosed aspects or embodiments of the invention, even though not specifically shown in the drawings or described in the text.

The various modules described herein can be implemented by software executing on a processor, hardware, firmware, or any combination of the three. When the modules are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various modules, as described herein, may be performed by one unit, or divided up among different components, each of which may be implemented in turn by any combination of hardware, software that is executed on a processor, and firmware. When divided up among different components, the components may be centralized in one location or distributed across system 300 for distributed processing purposes. The execution of the various modules results in methods that perform the processes described above for the various modules and controller 360.

Thus, a processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives and other physical storage mediums.

In view of this disclosure, instructions used in any part of or all of the processes described herein can be implemented in a wide variety of computer system configurations using an operating system and computer programming language of interest to the user.

Herein, first, second, etc. are used as adjectives to distinguish between elements and are not intended to indicate a number of elements. Also, top, bottom, and side are used as adjectives to aid in distinguishing between elements as viewed in the drawings, and to help visualize relative relationships between the elements. For example, top and bottom surfaces are first and second surfaces that are opposite and removed from each other. A side surface is a third surface that extends between the first and second surfaces. Top, bottom, and side are not being used to define absolute physical positions.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

What is claimed is:

1. An apparatus comprising:
   a non-zero degree endoscope comprising a body, a distal portion, and an image capture unit, the distal portion including a distal face; the distal portion being connected to the body, and the distal portion comprising a lengthwise axis, the distal face being at a fixed angle to the lengthwise axis of the distal portion; and
   the image capture unit comprising a zero degree lens stack, the zero degree lens stack having a non-folded optical path, the image capture unit having a lengthwise axis, and the image capture unit being mounted in the distal portion, the image capture unit being fixed in position with the lengthwise axis of the image capture unit intersecting the lengthwise axis of the body to define a non-zero degree angle and with the zero degree lens stack positioned to receive light incident on the distal face.

2. The apparatus of claim 1, wherein the non-zero degree angle is an acute non-zero degree angle.

3. The apparatus of claim 2, wherein the acute non-zero degree angle is a thirty degree angle.

4. The apparatus of claim 1, wherein the non-zero degree endoscope is a non-zero degree stereoscopic endoscope including the image capture unit and a second image capture unit, wherein the second image capture unit is substantially identical to the image capture unit.

5. The apparatus of claim 1, the image capture unit further comprising a window positioned proximal to the zero degree lens stack.

6. The apparatus of claim 1, the image capture unit further comprising an image sensor mounted in the image capture unit proximal to the zero degree lens stack.

7. The apparatus of claim 1, the image capture unit further comprising a stop positioned adjacent to a distal end of the zero degree lens stack.

8. The apparatus of claim 1, the zero degree lens stack comprising a distal lens, the distal lens comprising a filter embedded within the distal lens.

9. The apparatus of claim 1, further comprising a camera retainer mounted within the distal face of the non-zero degree endoscope, the camera retainer being configured to maintain the image capture unit within the distal portion, and the camera retainer having a first surface and a second surface, the first surface contacting the image capture unit and the second surface being aligned with the distal face of the body.

10. An endoscope comprising:
    a body;
    a distal portion connected to the body, the distal portion comprising a proximal end, a distal end, a distal face of the distal end, and a lengthwise axis extending between the proximal end and the distal end, the distal face being at a fixed angle to the lengthwise axis; and
    an image capture unit including an image forming lens assembly and an image sensor, the image forming lens assembly comprising a non-folded optical path between an entry location of light into the image forming lens assembly and the image sensor, and the image capture unit being mounted in a fixed position of the distal end of the distal portion at an angle to the lengthwise axis with the image forming lens assembly positioned to receive light incident on the distal face.

11. The endoscope of claim 10, the angle being an acute angle larger than zero degrees.

12. The endoscope of claim 11, wherein the acute angle is a thirty degree angle.

13. The endoscope of claim 10, the angle being a zero degree angle.

14. The endoscope of claim 10, wherein the endoscope is a stereoscopic endoscope including the image capture unit and a second image capture unit, wherein the second image capture unit is substantially identical to the image capture unit.

15. The endoscope of claim 10, the image capture unit further comprising a window positioned proximal to the image forming lens assembly.

16. The endoscope of claim 10, the image capture unit further comprising a stop positioned adjacent to a distal end of the image forming lens assembly.

17. The endoscope of claim 10, the image forming lens assembly comprising a distal lens, the distal lens comprising a filter embedded within the distal lens.

18. The endoscope of claim 10, further comprising a camera retainer mounted within the distal face of the distal portion, the camera retainer being configured to maintain the image capture unit within the distal portion, and the camera retainer having a first surface and a second surface, the first surface contacting the image capture unit and the second surface being aligned with the distal face of the body.

19. A family of endoscopes comprising:
a zero degree endoscope including a first body, a first distal portion, and a first image capture unit, the first distal portion being connected to the first body, the first distal portion having a first lengthwise axis, the first image capture unit having a second lengthwise axis, the first image capture unit being mounted in the first distal portion with the second lengthwise axis of the first image capture unit substantially parallel to the first lengthwise axis of the distal portion; and
a non-zero degree endoscope including a second body, a second distal portion, and a second image capture unit, the second distal portion being connected to the second body, the second distal portion having a third lengthwise axis, the second image capture unit having a fourth lengthwise axis, the second image capture unit being mounted in the second distal portion of the non-zero degree endoscope with the fourth lengthwise axis of the second image capture unit intersecting the third lengthwise axis of the second distal portion at a non-zero angle, the first and second image capture units having nearly identical non-folded optical paths between an entry location of light into each image capture unit and an imager of each image capture unit, and the first body being different from the second body.

20. The family of endoscopes as in claim 19, wherein each of the zero degree endoscope and the non-zero degree endoscope is a stereoscopic endoscope.

* * * * *